US008133868B2

(12) United States Patent
Neu

(10) Patent No.: US 8,133,868 B2
(45) Date of Patent: *Mar. 13, 2012

(54) DIPEPTIDES FOR PREVENTION OF MUSCLE BREAKDOWN AND MICROBIAL INFECTION

(75) Inventor: Josef Neu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 449 days.

This patent is subject to a terminal disclaimer.

(21) Appl. No.: 12/253,590

(22) Filed: Oct. 17, 2008

(65) Prior Publication Data

US 2009/0082283 A1 Mar. 26, 2009

Related U.S. Application Data

(63) Continuation of application No. 10/704,936, filed on Nov. 10, 2003, now Pat. No. 7,855,181, which is a continuation of application No. 09/636,491, filed on Aug. 11, 2000, now abandoned.

(60) Provisional application No. 60/149,369, filed on Aug. 13, 1999.

(51) Int. Cl.
*A61K 38/05* (2006.01)
*A01N 45/00* (2006.01)

(52) U.S. Cl. ...................... 514/21.91; 530/300; 514/168

(58) Field of Classification Search .................. None
See application file for complete search history.

(56) References Cited

U.S. PATENT DOCUMENTS

| 4,187,216 | A | * | 2/1980 | Hassall et al. ................ 548/538 |
| 4,340,592 | A |   | 7/1982 | Adibi |
| 5,189,016 | A |   | 2/1993 | Madsen et al. |
| 5,561,111 | A |   | 10/1996 | Guerrant et al. |
| 5,576,351 | A |   | 11/1996 | Yoshimura et al. |
| 6,051,270 | A |   | 4/2000 | Monte |
| 6,126,939 | A |   | 10/2000 | Eisenbach-Schwartz et al. |
| 7,148,199 | B2 | * | 12/2006 | Neu et al. ..................... 514/13.3 |
| 7,754,692 | B2 | * | 7/2010 | Neu et al. ...................... 514/1.3 |
| 7,855,181 | B2 | * | 12/2010 | Neu ............................ 514/21.91 |

FOREIGN PATENT DOCUMENTS

| DE | 19856789 A1 | 6/2000 |
| EP | 0 087 750 82 | 9/1983 |
| EP | 0 087 751 B1 | 9/1983 |
| EP | 0 182 356 A3 | 5/1986 |
| JP | 21 19762 | 5/1990 |
| JP | 2119762 | * 5/1990 |
| JP | 02119762 | 5/1990 |
| JP | 08 295633 | 11/1996 |
| WO | WO 98/09985 | 3/1998 |

OTHER PUBLICATIONS

Berse, 1960, Can. J. Chem., 38, 1946-1950.*
[Retrieved from]: http://www.chem.ucla.edu/harding/tutorials/stereochem/calcs.html. 2 pages, 2011 [Retrieved on Apr. 7, 2011].*
Abidi, S. et al., "Influence of Molecular Structure on Half-life and Hydrolysis of Dipeptides in Plasma: Importance of Glycine as N-Terminal Amino Acid Residue," *Metabolism* (1986), vol. 35, No. 9, pp. 830-836.
Cynober, L., "New Nitrogen Substrates in Preoperative Nutrition of the Adult," *Ann Fr Anesth Réanim* (1995), vol. 14, No. 2, pp. 102-106.
Le Boucher et al, "Modulation of immune response with ornithine A-ketoglutarate in burn injury: an arginine or glutamine dependency?" *Nutrition* (1999), vol. 15, No. 10, pp. 773-777.
Matilla, Belén et al., "Effects of Parental Nutrition Supplemented with Glutamine Dipeptide on Liver Antioxidant and Detoxication Systems in Rats," *Nutrition* (2000), vol. 16, pp. 125-128.
Mattox et al., "Recent Advances: parental nutrition support," *Annals of Pharmacotherapy* (1995), vol. 29, No. 2, pp. 174-180.
Miyazawa, K. et al., "Amino-acids and Peptide in 7 Species of Marine Green Algae," *Journal of the Faculty of Fisheries and Animal Husbandry Hiroshima* (1976), vol. 15, No. 2, pp. 161-169.
Moinard et al., "Involvement of glutamine, arginine, and polyamines in the action of ornithine alpha-ketoglutarate on macrophage functions in stressed rats," *Journal of Leukocyte Biology* (2000), vol. 67, pp. 834-840.
Neu, Josef et al., "Glutamine nutrition and metabolism: Where do we go from here?" *The FASEB Journal* (1996), vol. 10, pp. 829-837.
Robinson et al., "Amino acid nutrition and immune function in tumour-bearing rats: a comparison of glutamine-arginine- and ornithine 2-oxoglutarate-supplemented diets," *Clinical Science* (1999), vol. 97, No. 6, pp. 657-669.

* cited by examiner

*Primary Examiner* — Cecilia J Tsang
*Assistant Examiner* — Satyanarayana R Gudibande
(74) *Attorney, Agent, or Firm* — Saliwanchik, Lloyd & Eisenschenk

(57) ABSTRACT

The subject invention provides dipeptides useful in promoting healthy muscle tissues as well as effective immune responses. The dipeptides of the subject invention are particularly advantageous because they are stable, bioavailable, and can be formulated in an aqueous solution.

11 Claims, No Drawings

DIPEPTIDES FOR PREVENTION OF MUSCLE BREAKDOWN AND MICROBIAL INFECTION

CROSS-REFERENCE TO RELATED APPLICATION

This application is a continuation of application Ser. No. 10/704,936, filed Nov. 10, 2003 now U.S. Pat. No. 7,855,181; which is a continuation of application Ser. No. 09/636,491, filed Aug. 11, 2000, now abandoned; which claims the benefit of U.S. Provisional Application No. 60/149,369, filed Aug. 13, 1999.

BACKGROUND OF THE INVENTION

Prevention or inhibition of muscle breakdown, and the facilitation of efficient muscle repair is of great interest to athletes, the elderly, and those with muscle-wasting conditions. A wide range of products and methods have been proposed for enhancing healthy muscle tissues and enhancing athletic performance. Existing compositions and methods which are available for these purposes suffer from a variety of shortcomings. These shortcomings range from potentially dangerous side affects, to a lack of bioavailability and difficulty in formulation and/or administration.

It is well known that proteins are converted to amino acids in the digestive system and that the resulting amino acids are used by the body for growth and development. In certain medical situations a patient may be unable to receive proteins. In these situations patients have been given free amino acids. Free amino acids, however, are sometimes not tolerated well by patients and may cause diarrhea and dehydration. Also, the free amino acids may be unstable and/or difficult to formulate.

It has been observed that the body can more effectively absorb certain small molecules called dipeptides or tripepetides. These molecules consist of, for example, two to three amino acids. It has been observed, for example, that peptides containing the amino acid residue glycine in the N-terminal position are readily assimilable. See for example, U.S. Pat. No. 4,340,592.

European Patent Application No. 0,182,356 discloses a nutritional composition containing at least one oligopeptide consisting of a dipeptide or a tripeptide wherein the N-terminal amino acid residue is selected from the class consisting of alanine, lysine and arginine.

One group conducting research in this area concluded that glycine is generally superior to other amino acids as the N-terminal amino acid residue in a dipeptide. This superiority was attributed to a greater fraction of such an intravenously administered dipeptide reaches the tissues. S. Adibi et al., *Influence of Molecular Structure on Half-life and Hydrolysis of Dipeptides in Plasma: Importance of Glycine as N-Terminal Amino Acid Residue,* 35 Metabolism 850, 835 (1986).

Two European patents, 0,087,751 and 0,087,750 disclose water-soluble peptides. The '751 patent discloses a method to parenterally administer low water-soluble amino acids. Two amino acids, tyrosine and cystine, individually have low solubility in water. These amino acids, however, are clinically useful and, therefore, it was desirable to find an effective formulation. The '751 patent describes an infusion method which involves bonding these relatively insoluble amino acids to the amino acid lysine to produce a tripeptide.

The '750 patent discloses the infusion of glutamine as a derivative substituted by α-aminoacyl residues on the a amino group. That is, glutamine is in the "c-terminal" position, in that its alpha amino nitrogen becomes part of the peptide bond with the other amino acid. The preferred dipeptide preparation disclosed in the '750 patent is alanyl-glutamine. The aminoacylation of glutamine is reported to achieve a stabilization of the terminal amide group.

Experiments involving the use of total parenteral nutrition (TPN) containing glycyl-glutamine dipeptides, however, suggest potential adverse effects of the TPN formulation containing glycyl-glutamine (U.S. Pat. No. 5,189,016).

Two commercially available dipeptides of glutamine are Dipeptiven, which is an alanyl-glutamine (Fresenius Laboratories, Germany) and Glamin (Pharmacia and Upjohn Laboratory, Sweden), which is an amino acid solution containing glycyl-glutamine dipeptide. To this date, there are no studies of the arginyl-L-glutamine dipeptide.

It is well known that nutrition can impact the functioning of the immune system. Proper nutrition can promote healthy immune responses. There are many aspects to the immune response of humans and animals. One component of the immune response is mucosal immunity. Mucosal immunity provides a first line of defense for the body against a broad range of pathogens.

There remains a great need in the art for compositions and methods which promote healthy muscle tissue, reduce muscle deterioration, and/or promote a healthy immune system.

BRIEF SUMMARY OF THE INVENTION

In one embodiment, the subject invention provides materials and methods useful in promoting healthy muscle tissue. The promotion of healthy muscle tissue according to the subject invention is particularly advantageous for athletes and others engaging in rigorous physical exertion and/or training. The promotion of healthy muscle tissue according to the subject invention is also advantageous for the treatment and/or prevention of muscle wasting conditions. This is particularly advantageous for critically ill hospitalized patients including neonates.

The compositions of the subject invention are also useful in promoting mucosal immunity. Such immunity, which is often typified by an IgA response, can be a critical defense against a variety of human and animal pathogens. These pathogens may be, for example, bacteria, viruses, or parasites.

In a preferred embodiment of the subject invention, the amino acids arginine and glutamine are combined as the dipeptide arginyl-glutamine in order to provide beneficial effects in a safe, easily absorbable formulation. The dipeptide of the subject invention promotes healthy muscle tissue and an advantageous immune response. The dipeptide of the subject invention is also advantageous because it is safe for human or animal consumption and can be readily formulated in an aqueous solution for internal consumption.

The compositions of the subject invention can be used in a variety of situations where it is desired to promote healthy muscle tissue. For example, the dipeptides of the subject invention can be used in medical applications to aid critically ill patients. Also, the arginyl-glutamine dipeptide can be applied to enhance athletic performance.

The compositions can also be used to promote a healthy immune system in humans or animals. This is particularly advantageous for patients and hospital workers, or others who may be exposed to pathogens.

These peptides of the subject invention can be administered as one component of a nutrient composition. The use of these peptides, compared to the administration of equivalent amounts of the free amino acids, cause a decrease in osmolarity of the solution, facilitate the administration of amino acids having low water solubility, and stabilize heat unstable amino acids such as glutamine. The aqueous solution is suitable for intravenous feeding or for intragastrointestional administration. The aqueous solution itself may contain other nutrient additives such as fats, glucose, mono- or oligo-saccharides, minerals, trace elements and/or vitamins.

DETAILED DISCLOSURE OF THE INVENTION

The present invention relates to nutrient compositions containing dipeptides and methods for administering the same. Advantageously, the subject invention provides a dipeptide having water solubility, stability to sterilization, long-term stability, and bioavailability for humans and animals. A preferred embodiment of the present invention provides a nutrient composition comprising an aqueous solution having at least one arginyl-glutamine dipeptide.

Among the advantages of the dipeptide of the subject invention overthe existing alanyl-glutamine and glycyl-glutamine dipeptides is that the arginine moiety is particularly advantageous because it is a creatine phosphate precursor, a stimulator of immune function, a stimulator of growth hormone production and, in combination with glutamine, is particularly useful in strengthening mucosal immune defenses.

In one embodiment of the subject invention the arginyl-glutamine dipeptides described herein are useful for promoting healthy muscle tissue. Thus, these dipeptides can be used by athletes or others who are undergoing training or other rigorous physical exertion. The dipeptide compositions of the subject invention can also be used to promote muscle repair and maintenance in hospital or hospice patients, or other individuals subject to muscle deterioration.

In a further embodiment, the subject invention provides materials and methods for enhancing the immune system functioning of humans and animals. In this embodiment, compositions which comprise the arginyl-glutamine dipeptide are administered to people or animals who could benefit from an improved immune response. Specifically, the dipeptides of the subject invention can be used to enhance mucosal immunity. This enhancement of mucosal immunity reduces the risk of infection by a variety of pathogens including bacteria, viruses, and parasites.

In view of the muscle maintenance characteristics of the arginyl-glutamine dipeptide combined with its ability to stimulate an effective immune response, the compositions of the subject invention are particularly attractive for use in hospitals. For example, compositions containing the dipeptide of the subject invention can be used to maintain muscle mass in inactive patients while having the added benefit of reducing susceptibility to hospital acquired infections in patients.

In accordance with the teachings provided herein, aqueous clinical nutrient compositions can be prepared which include at least one arginyl-glutamine dipeptide. The dipeptide can be added to enteral or parenteral formulations of either complete or incomplete nutritional content. Each dipeptide has an N-terminal amino acid which is arginine. The C-terminal amino acid is glutamine.

The concentration of the dipeptide in the aqueous solution can be, for example, from about 0.1 to about 25.0 percent by weight. In addition to dipeptides, the clinical nutritional solution can contain, for example, dextrose, liquid emulsions, vitamins, minerals and trace elements. The selection of the particular dipeptide formulation depends upon the particular use.

Dipeptide additives such as single or multiple entities, as well as a total nutritional formulation which contains dipeptides as one component among many are contemplated by this invention.

The aqueous dipeptide formulation may be ingested orally along with other nutrients such as conventional foods or prepared vitamins, fats, glucose or other mono-saccharides, oligosaccharides, minerals and trace elements. For parenteral administration, a supply of the dipeptide solution may be merged through a Y-connection with a supply of glucose solution or other parenteral solutions. The dipeptide solutions may be mixed with glucose solutions and/or other parenteral solutions to create a mixture which may be administered parenterally. The administration of dipeptides rather than free amino acids allows administration of the same amount of amino acid residue in solutions which are less hypertonic and therefore can be introduced into peripheral veins.

The dipeptides of the subject invention can be readily synthesized and/or formulated by a person skilled in the art having the benefit of the instant disclosure. Alternatively, the dipeptides can be purchased commercially from, for example, Bachem Biosciences, Inc. which sells the H-Arg-Glu-OH salt.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. An aqueous, enteral nutrient formulation comprising an arginyl-glutamine dipeptide and at least one additive, wherein the arginine residue is the amino terminus of said dipeptide and the glutamine residue is the carboxy terminus of said dipeptide, and wherein the additive is selected from the group consisting of vitamins, minerals, trace elements, fats, monosaccharides and oligosaccharides.

2. The peptide composition, according to claim 1, wherein the concentration of said dipeptide is from about 0.1% to about 25.0% by weight of said formulation.

3. The peptide composition, according to claim 1, wherein said monosaccharide is glucose.

4. A method for increasing healthy muscle tissue in a human or animal, said method comprising administering to a human or animal in need of such treatment an effective amount of an aqueous enteral nutrient formulation comprising an arginyl-glutamine dipeptide and at least one additive, wherein the arginine residue is the amino terminus of said dipeptide and the glutamine residue is the carboxy terminus of said dipeptide, and wherein the additive is selected from the group consisting of vitamins, minerals, trace elements, fats, monosaccharides and oligosaccharides.

5. The method, according to claim 4, wherein said human or animal has undergone, is undergoing, or will undergo physical exertion or training.

6. The method, according to claim 4, wherein said human or animal is in need of maintenance of muscle mass.

7. The method, according to claim 6, wherein said human or animal is hospitalized.

8. The method, according to claim 7, wherein said hospitalized human or animal is a neonate.

9. A method for increasing immunity to pathogens in a human or animal, said method comprising administering to a human or animal in need of such treatment an effective amount of an aqueous, enteral nutrient formulation comprising an arginyl-glutamine dipeptide and at least one additive, wherein the arginine residue is the amino terminus of said dipeptide and the glutamine residue is the carboxy terminus of said dipeptide, and wherein the additive is selected from the group consisting of vitamins, minerals, trace elements, fats, monosaccharides and oligosaccharides.

10. The method, according to claim 9, wherein said human or animal is an employee, worker or patient in a hospital or medical facility.

11. The method, according to claim 9, wherein said immunity is mucosal immunity.

* * * * *